United States Patent [19]

Stotts

[11] Patent Number: 4,663,701
[45] Date of Patent: May 5, 1987

[54] VOLTAGE LEVEL SHIFTER

[75] Inventor: Lawrence J. Stotts, Lake Jackson, Tex.

[73] Assignee: Intermedics, Inc., Angleton, Tex.

[21] Appl. No.: 761,977

[22] Filed: Aug. 2, 1985

[51] Int. Cl.⁴ .......................................... H02M 3/155
[52] U.S. Cl. ..................................... 363/60; 307/264; 307/279
[58] Field of Search ................... 363/60; 128/419 PS; 307/264, 279

[56] References Cited

U.S. PATENT DOCUMENTS

| | | | |
|---|---|---|---|
| 3,942,047 | 3/1976 | Buchanan | 363/60 X |
| 4,039,862 | 8/1977 | Dingwall et al. | 307/279 X |
| 4,061,929 | 12/1977 | Asano | 363/60 X |
| 4,344,003 | 8/1982 | Harmon et al. | 363/60 X |
| 4,486,670 | 12/1984 | Chan et al. | 307/279 X |
| 4,494,018 | 1/1985 | Clemen et al. | 307/264 X |

Primary Examiner—Patrick R. Salce
Assistant Examiner—Marc S. Hoff
Attorney, Agent, or Firm—Willian Brinks Olds Hofer Gilson & Lione Ltd.

[57] ABSTRACT

An improved voltage level shifter circuit employs pairs of P and N-channel devices which are operated in response to control signals to generate a voltage shifted output signal that corresponds in timing and polarity to an input data signal. The P and N-channel devices interact in latched pairs to maintain logic levels for the output signal. The P-channel and N-channel devices of each pair are disconnected prior to each logic level change for the output signal so that the devices of each pair do not oppose one another in changing the logic level of the output signals.

20 Claims, 5 Drawing Figures

VOLTAGE LEVEL SHIFTER

TECHNICAL FIELD

The invention relates to a voltage shifting logic circuit which receives signals at one voltage level and generates corresponding signals at a predefined greater voltage level. More particularly, the invention relates to such a circuit which is implemented with CMOS logic, has relatively low current requirements and is suitable for reliably shifting voltage levels in an implanted heart pacemaker.

BACKGROUND OF THE INVENTION

In modern logic circuits it is often necessary to apply signals of a relatively low voltage level to energize and operate one type of electrical component, for example digital logic components, and signals of a relatively higher voltage level to operate and energize other types of related components, for example capacitors. In practice, it is therefore often necessary to apply a signal which has different voltage levels at different portions of a circuit.

Modern implantable heart pacemakers provide one example of relatively sophisticated electronic devices which require operational signals at different voltage levels. In such a device, it is not unusual to require a low voltage level of for example 2 volts to energize certain portions of a complex logic circuit and a greater voltage of for example 8 volts to activate other portions of the circuit. Thus, relatively low level voltage signals are applied to energize and operate TTL logic circuits which control the pacemaker, while more powerful signals are required to energize capacitors which stimulate the heart.

Implanted heart pacemakers must operate over a period of years on power supplied by relatively small batteries disposed within the housing of the pacemaker. It is therefore necessary to provide a pacemaker which is reliable, stable and which also consumes a relatively low dynamic current in order to reduce the drain on the batteries. As a practical matter, the pacemaker should also have a relatively low static current consumption so that the drain on the batteries is minimized when the pacemaker is in a quiescent or rest state.

Pacemakers and like devices have employed CMOS level shifting circuits to provide the bilevel voltages required in operation. Such circuits have typically required relatively large and powerful P-channel transistor switching devices to operate with lower power P-channel and N-channel digital logic devices. The use of the relatively large and powerful P-channel devices results in a relatively large current drain when the level shifter circuit changes state. The relatively high capacitance of the large P-channel devices also tends to reduce the speed of operation of the level shifting circuit. Moreover, the relatively large physical size of the devices is a disadvantage in apparatus, for example heart pacemakers, which must be made as small as possible.

Finally, in existing level shifting circuits, the quiescent or rest state of the circuit is characterized by a perceptible leakage current which provides a constant drain on the power supply of the circuit. This is a serious disadvantage for self-contained powered apparatus such as heart pacemakers.

Accordingly, it is an object of the invention to provide a level shifting logic circuit which operates without requiring the use of relatively large P-channel devices.

A further object of the invention is to provide such a circuit which operates with relatively small P-channel and N-channel transistor devices to minimize the size and power consumption of the circuit.

A further object of the invention is to provide a level shifting circuit which minimizes the capacitance of operational components of the circuit and which therefore increases the speed of operation of the circuit.

Another object of the invention is to provide such a level shifting circuit which minimizes leakage current in the quiescent or rest state and which therefore reduces the power consumption of the circuit and promotes a longer life for any self-contained power supply for the circuit.

A further object of the invention is to provide a relatively low power and relatively fast level shifting circuit which is well-suited for shifting the voltage level of operational signals in an implanted heart pacemaker.

These and other objects of the invention will become apparent from a review of the specification which follows and of the drawings which are described hereafter.

SUMMARY OF THE INVENTION

In order to achieve the objects of the invention and to overcome the problems of the prior art, the improved voltage level shifting circuit of the invention utilizes cross-connected N-channel and P-channel CMOS field effect transistors to achieve a voltage level-shifting operation. The transistors are controlled so that the P-channel and N-channel devices do not pull against one another when they are configured to generate a voltage shifted signal which corresponds in polarity and timing to an input data signal.

DETAILED DESCRIPTION OF PREFERRED EMBODIMENT

The remaining portion of this specification will describe a preferred embodiment of the level shifter of the invention when read in conjunction with the attached drawings, in which like reference characters identify identical apparatus.

Figure 1A:
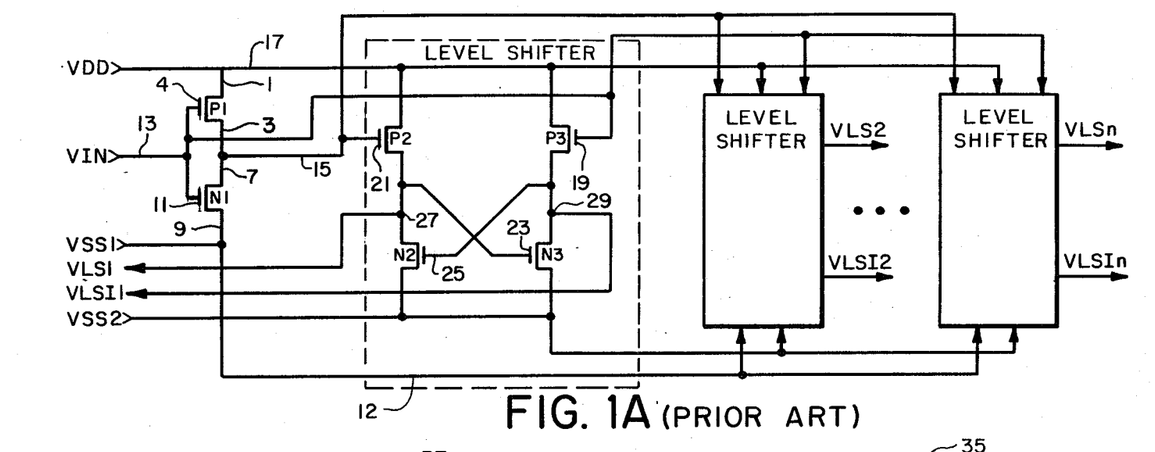
FIG. 1A illustrates a prior art CMOS level shifting circuit.

FIG. 1 illustrates a prior art circuit which shifts the voltage swing of an input signal VIN from a voltage level defined between a voltage reference VSS1 and a voltage VDD to a corresponding output signal VLS which has a greater voltage swing from a reference VSS2 to the voltage VDD.

It will be appreciated by those skilled in the art that the circuit of FIG. 1A is comprised of metal oxide semiconductor (MOS) field-effect transistors (FET's). The circuit of FIG. 1A employs both N-channel and P-channel field-effect transistors which are interconnected to provide push-pull complementary digital circuits. The P-channel field-effect transistors of FIG. 1A are designated with a "P" and the N-channel transistors are designated with an "N". Thus, the transistors P1, P2 and P3 of FIG. 1A are P-channel devices, and the transistors N1, N2 and N3 are N-channel devices.

The P-channel and N-channel field-effect transistors operate as solid state switches to conduct current between source and drain leads in accordance with a voltage which is applied to a gate lead. Thus, for example, the transistor P1 will conduct current between its source 1 and drain 3 when a low logic voltage signal is applied to its gate 4. In the conducting state the transistor P1 is said to be turned on. When a high logic voltage signal is applied to the gate 4, the transistor P1 is turned off so that there is substantially an open circuit between the source 1 and drain 3.

The opposite operation is provided for N-channel transistors, for example the N-channel device N1. In operation, the device N1 is turned on to conduct current between its source 7 and drain 9 in response to a high voltage logic signal applied to its gate 11. The device N1 is turned off to stop conducting current in response to a logic low signal applied to its gate 11.

The operation of the circuit of FIG. 1A will be described with respect to a level shifter 12 wherein a positive voltage VDD defines a high logic level and further defines the positive voltage swing of an input signal VIN of FIG. 1B which is provided as a data input at an input line 13. A lower voltage signal VSS1 defines a low logic level and further defines the low point of the voltage swing of the input signal VIN.

Figure 1B:
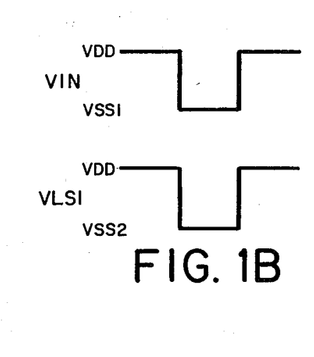
FIG. 1B illustrates input and output signals for the circuit of FIG. 1A.

An output signal VLS1 is illustrated at FIG. 1B. The VLS1 signal corresponds in timing to the signal VIN but has a greater voltage swing which the level shifter 12 provides between the positive voltage VDD and a voltage VSS2 which is less than the voltage VSS1.

In operation, the transistors P1 and N1 of FIG. 1A form an inverter which generates a signal on a line 15 that is inverted in polarity with respect to the signal VIN applied at line 13. Thus, if the signal VIN is high, then the device P1 is turned off to provide an open circuit between the VDD line 17 and the inverter output line 15. However, the high voltage level on the line 13 causes the transistor N1 to be turned on and thus causes the low voltage VSS1 to be applied to the line 15. It should therefore be appreciated that the conducting transistor N1 provides a low signal on the line 15 which is opposite in polarity to the relatively high voltage of the signal VIN on the line 13. When the VIN signal drops to the low voltage VSS1, the transistor P1 is turned on and the transistor N1 is turned off. When P1 is turned on, the high voltage VDD is applied to the line 15. Thus, the voltage on the line 15 is the opposite or complement of the voltage of the signal VIN on the input line 13.

The input signal VIN is applied to the gate 19 of a P-channel transistor P3 and the inverted signal of the line 15 is applied to the gate 21 of a P-channel device P2. If the input signal VIN is a logic high (i.e., when the signal is equal to VDD), the transistor P3 is turned off and the transistor P2 is turned on in response to the inverted logic low signal of line 15.

When P2 is turned on, it conducts to apply the high voltage VDD to the gate 23 of an N-channel transistor N3. The high voltage on the gate 23 turns on N3 so that it conducts to apply the low voltage VSS2 to the gate 25 of an N-channel device N2. The low voltage on the gate 25 turns off N2. The conducting device P2 and the nonconducting device N2 apply the high voltage VDD to a circuit node 27 for the output signal VLS. The circuit of FIG. 1A will remain latched to provide a high output signal VLS for as long as a high input signal VIN is applied at the line 13. In this latched state both the input signal VIN and output signal VLS1 have a voltage value of VDD. In this steady state the circuit of FIG. 1A exhibits a classical low static current consumption which is characteristic of complementary metal oxide semiconductor circuits (CMOS).

An inverted output signal VLSI1 is provided at a node 29 of the circuit of FIG. 1A. The signal VLSI1 is therefore low when the signal VLS1 at node 27 is high. The low VLSI1 signal at node 29 is provided because P3 is turned off and N3 is turned on, as discussed above. The conducting N3 transistor applies the lowest voltage signal VSS2 to the node 29. Thus, the inverted output signal VLSI1 has the lowest possible voltage of VSS2 when the output signal VLS1 is a positive voltage VDD at node 27.

It should be appreciated that the combination of the transistors P2 and N2 will provide an output signal VLS1 at node 27 which corresponds to the polarity of the input signal VIN applied on line 13. The transistors P3 and N3 are operated in an inverted, latching relation with the devices P2 and N2 and therefore provide a corresponding inverted output signal VLSI1 at node 29.

When a low voltage VSS1 is applied by VIN at line 13, P3 is turned on and the inverted gate voltage at line 15 turns device P2 off. At the point at which the device P3 is turned on, the associated paired device N3 is still on. Accordingly, P3 attempts to conduct to apply a positive voltage VDD at the circuit node 29 at a time when N3 is conducting and therefore ties the circuit node 29 to the low voltage VSS2. In order for a switching operation to take place, the device P3 must be "stronger" than the device N3 in order to pull up the node 29 and latch the shifter against the conducting state of N3.

The "strength" of P3 is determined by its physical size, capacitance and current sinking ability with respect to N3. In practice, it has been found that P3 can overcome N3 if it has a size of 40 with respect to a size of 0.5 for N3. Those skilled in the art will understand that the size of a CMOS transistor is determined by the ratio of Z/L, where Z is the gate size of the transistor and L is the gate length of the transistor. A size of 40 for P3 is achieved by providing a 200 micron gate width and a 5 micron gate length. The size of N3 is achieved by providing a 5 micron gate width and a 10 micron gate length. The larger size of the Z/L ratio for P3 allows P3 to draw a greater current than N3. However, P3 has a relatively greater capacitance than N3 and therefore switches more slowly than N3.

As a result of the larger size of P3, when P3 is turned on at the time that N3 is turned on, the stronger P3 device conducts to pull the circuit node 29 to the high VDD voltage, thus shorting the device N3 and turning it off. The logic high forced at the node 29 applies a logic high signal to the gate 25 of N2 and therefore turns N2 on. When N2 is turned on, it conducts to apply the negative voltage VSS2 to the circuit node 27 and to the gate 23 of N3. The logic low on the gate 23 thus turns off N3. The output signal VLS1 will thus be forced to a logic low voltage VSS2, while the inverted output signal VLSI1 at the node 29 will be forced to a logic high voltage VDD by the conducting device P3. The devices of the level shifter 12 will be latched in the indicated operational states until the input signal VIN again returns to a high voltage VDD, thus turning off P3, turning on P2 and switching the logic levels of the output signal VLS1 and VLSI1.

As described with respect to the devices P3 and N3, P2 is provided with a size of approximately 40 to overcome the device N2 which has a size of 0.5. The size differential is required when P2 and N2 operate together to change the state of the level shifter in the manner previously described with respect to the devices P3 and N3.

It should be understood that in order for the level shifter to change state, a P-channel device (P2,P3) must totally overpower a conducting N-channel device (N2,N3). In a typical circuit, for example such as is used for signal level shifting in heart pacemakers, it is desirable to provide a level shift of, example, from 2 volts to 8 volts. The above-indicated size for the devices P2,P3 in relation to the devices N2,N3 is provided to achieve such a voltage shift. The P devices must be much greater in size in order to ensure a complete level transition for each switching operation of the level shifter. An incomplete level transition would result in a very high current drain and hence early failure for the power supply of an implanted device such as a heart pacemaker.

The large physical size of the P devices is a disadvantage, because it limits the miniaturization which can be achieved with the device in which it operates. This is particularly true for a heart pacemaker, which will require many level shifting circuits as illustrated in FIG. 1A. The relatively large sized P devices also have a substantial capacitance and therefore switch more slowly than is desirable for microprocessor-driven circuits such as are employed in modern heart pacemakers.

The circuit of FIG. 1A has the additional disadvantage of simultaneously turning on P-N pairs at the time that the output of the circuit changes state. The circuit generates an undesirable current spike at these points of transition. As a result of this current spiking, the current load presented to the voltage source for the circuit increases as the switching frequency of the circuit increases. This current spiking provides an undesirable current drain at the relatively high switching rates of circuits employed with heart pacemakers.

The circuit of FIG. 1A thus has the desirable low static current consumption which is characteristic of CMOS circuits, but it has an undesirably large dynamic current drain resulting from current spiking during switching of the level shifters. Also, the circuit has a rather large physical size because of its use of relatively large P-type devices.

Figure 2:
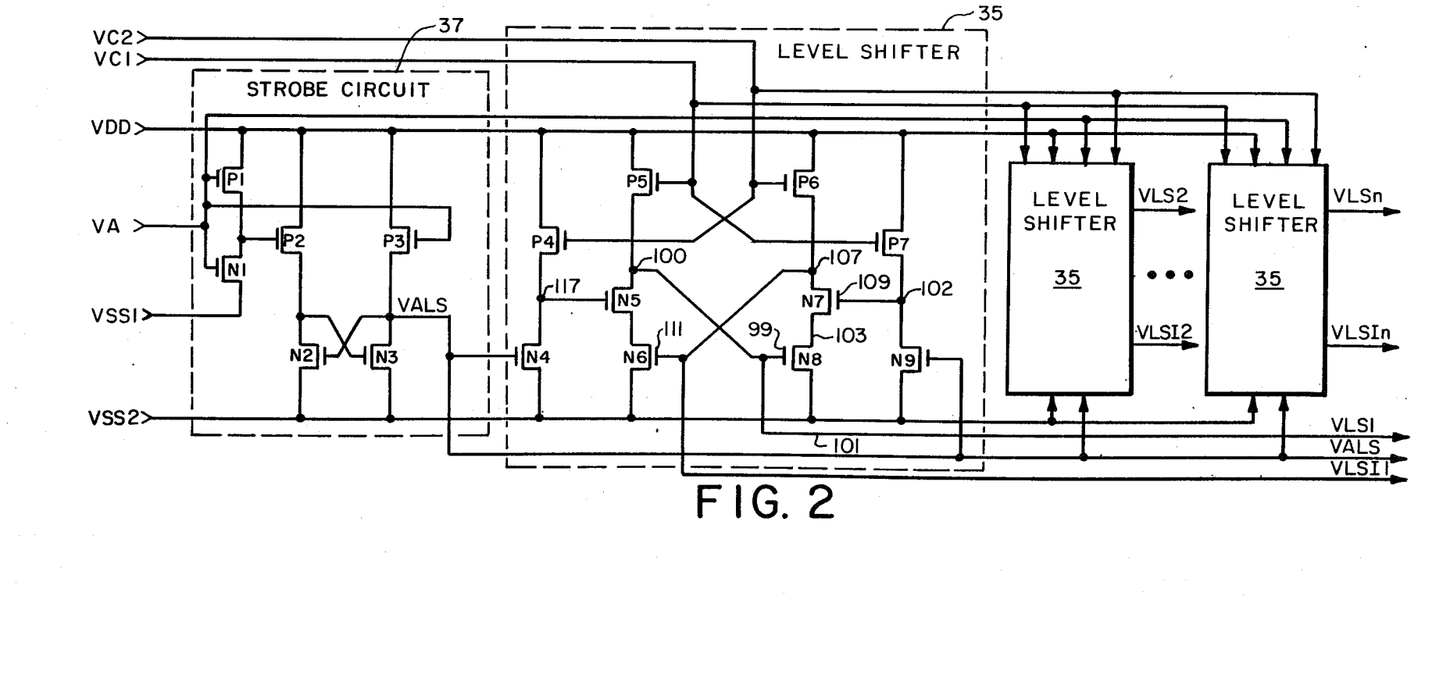
FIG. 2 illustrates a diagram of a CMOS level shifting circuit in accordance with the invention.

FIG. 2 illustrates an embodiment of a level shifting circuit in accordance with the invention. The circuit does not require large field-effect transistor devices and further has a low dynamic current consumption with respect to the prior art circuit of FIG. 1A. The front-end strobe circuit 37 of FIG. 2 is a driver circuit which operates a plurality of associated level-shifting stages 35. The front-end strobe circuit 37 operates in exactly the same manner as is described for FIG. 1A. Thus, the devices P2 and P3 are sized with a Z/L factor of 40, while the devices N2 and N3 are sized with a Z/L factor of 0.5. The advantage of the level shifting circuit of FIG. 2 is achieved by adding to the strobe circuit 37 level-shifting circuits which correspond to the illustrated circuit 35. The P-channel field-effect transistor devices P4, P5, P6 and P7 of FIG. 2 have a Z/L ratio of 10/5. The N-channel devices N4, N5, N6, N7, N8 and N9 have a Z/L ratio of 5/5. The P and N devices of the circuit 35 are thus relatively small in size and therefore have a relatively low capacitance, a relatively fast switching time and take up relatively little space. The savings in space is particularly apparent when multiple circuits 35 are driven by the circuit 37 to shift many voltage levels.

The circuit 37 provides a series of relatively narrow strobe pulses VALS to the string of level shifters 35. A control circuit of FIG. 3 generates timing signals for operating the strobe circuit 37 and level shifter circuits 35 of FIG. 2. FIG. 4 is a timing diagram of operational signals for the circuits of FIGS. 2 and 3.

The operation of the improved level shifters 35 may be best understood if it is initially noted that the P-channel devices P5,P6 and the N-channel devices N6,N8 generally respectively correspond to the devices P2,P3 and N2,N3 of the circuit of FIG. 1A. Thus, the devices P5,P6,N6,N8 operate generally in the manner described for the devices P2,P3,N2,N3 to provide a level shifting function. The improved operation of the circuit of FIG. 2 is achieved by the operation of the devices P4,P7,N4,N5,N7 and N9 which are controlled to selectively disconnect P6 from N8 and P5 from N6 whenever the state of the level shifter 35 is changed. The disconnected P-N pairs operate independently and therefore allow a level shift to occur without requiring P-channel devices (P5,P6) to overpower their associated N-channel devices (N6,N8). The level shifter circuits 35 therefore do not require oversized P-channel devices and also operate without requiring undesirably high dynamic current loads when the state of the shifters is changed.

Figure 3:
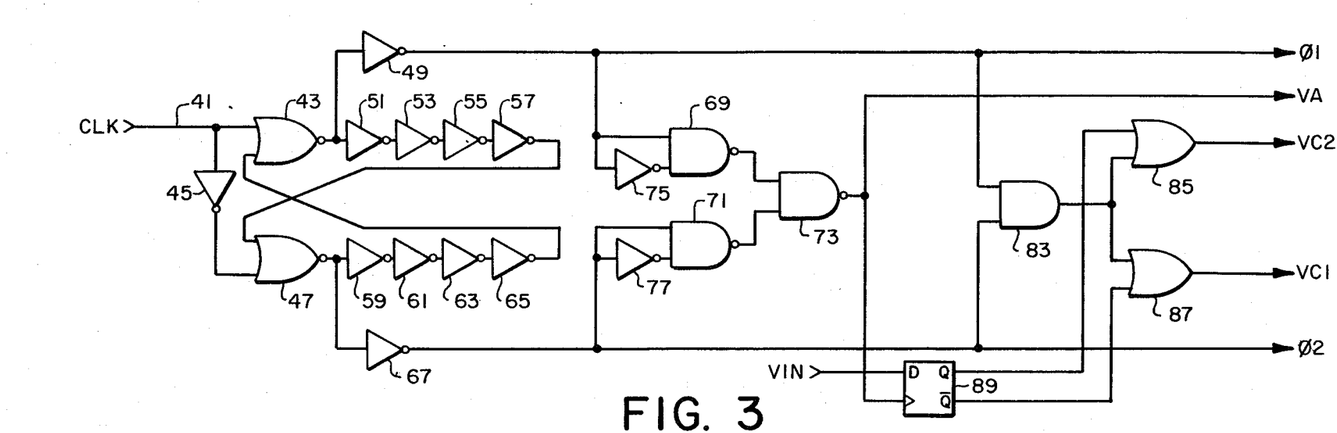
FIG. 3 illustrates a circuit for generating drive signals for the level-shifting circuit of FIG. 2.
Figure 4:
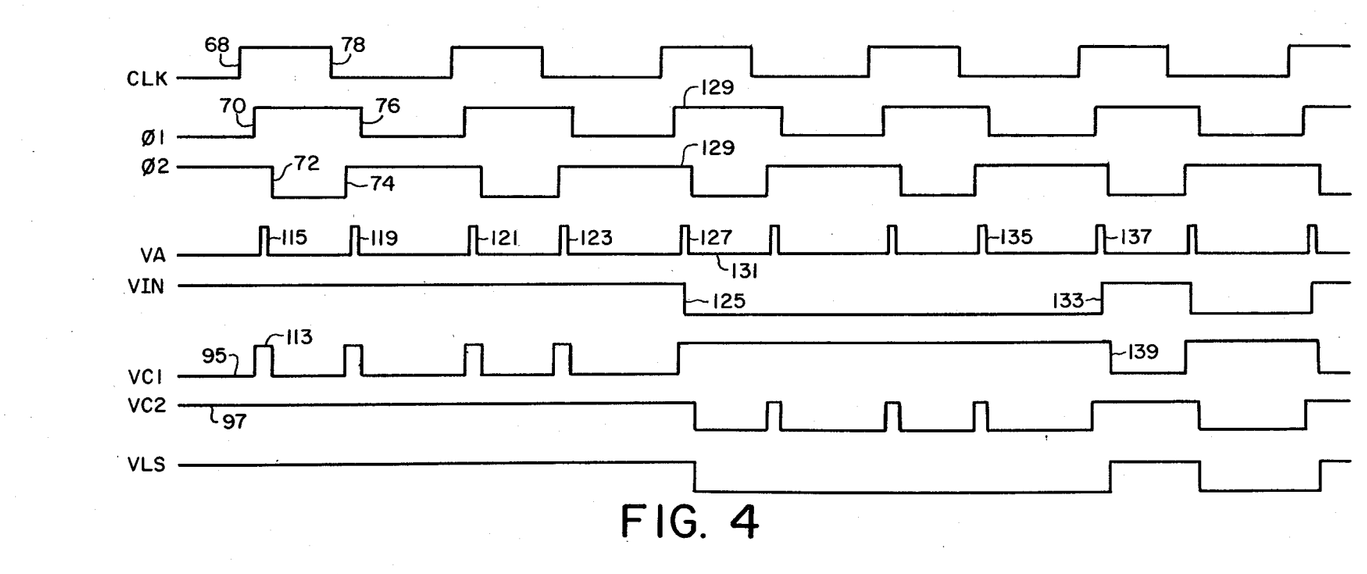
FIG. 4 illustrates a timing diagram of operational signals for the circuit of FIG. 2.

With reference to FIGS. 3 and 4, a clock signal is applied at 41 to provide timing for the control circuit. In a preferred embodiment of the invention a clock frequency of approximately 1 KHz. is employed. However, it should be understood that other clock frequencies may be used, without departing from the invention.

The clock pulses are passed to a NOR gate 43 and to an inverter 45 which transmits corresponding inverted clock pulses to a NOR gate 47.

If the clock pulse is high, the output of the NOR gate 43 is forced low and the low signal is applied to an output inverter 49 and a string of delay inverters 51-57. The last delay inverter 57 applies a delayed logic low signal to an input of the NOR gate 47. An opposite input of the NOR gate 47 receives a logic low signal from the inverter 45 and thus forces a high logic signal at the output of the inverter 47. The high output of the NOR gate 47 is applied through delay inverters 59-65 to the input of the NOR gate 43. The high output of the last delay inverter 65 latches the NOR gate 43 to hold a low at the output of the NOR gate.

For as long as the output of the NOR gate 43 remains low, the output inverter 49 generates a high phase signal ∅1 in delayed relation with respect to the clock signal. When the clock pulse eventually drops to a logic low, a logic high signal is applied by the inverter 45 to an input of the NOR gate 47 to force the output of the NOR gate to a logic low. After a delay determined by the inverters 59-65, the output of the NOR gate 43 is forced to a high logic level and the output of the inverter 49 drops to a low logic level. The output of the NOR gate 47 is applied to an output inverter 67 which generates an inverted signal ∅2.

With reference to the timing diagram of FIG. 4, it should be understood that the NOR gates 43,47 and associated inverters operate to generate a phase signal ∅1 which is delayed in time and is increased in pulse width with respect to as the clock signal but which maintains the same polarity of the clock signal. The indicated logic elements further generate the ∅2 phase signal which is inverted with respect to the clock signal and which falls within the positive pulse of the ∅1 phase signal.

The indicated timing relationship of the clock and the phase signals ∅1, ∅2 is achieved by the use of timing delays. Thus, the leading edge 70 of the ∅1 signal is delayed with respect to the leading edge 68 of the clock signal as a result of delays provided by the NOR gate 43 and its associated output inverter 49. The leading edge 72 of the ∅2 phase signal is delayed with respect to the leading edge 70 of the ∅1 phase signal as a result of a delay provided by the inverters 51–57, NOR gate 47 and the inverter 67. The trailing edge 74 of the ∅2 phase signal occurs before the trailing edge 76 of the ∅1 phase signal, because of a difference in the time delays of the components which generate the two signals. Thus, when the trailing edge 78 of the clock signal drops to a low logic level, the ∅2 phase signal will rise at 74 after a delay determined by the inverter 45, NOR gate 47, and the inverter 67. However, the trailing edge of the ∅1 phase signal will not drop from a high level to a low level until after a delay defined by the inverter 45, NOR gate 47, delay inverters 59–65, NOR gate 43 and inverter 49. The time delay operation of the circuit of FIG. 3 thus ensures that the leading edge of the phase signal ∅1 precedes the leading edge of the phase signal ∅2 and the trailing edge of ∅2 precedes the trailing edge of ∅1. Thus, the phase signals ∅1 and ∅2 are generated in a non-overlapping relationship. That is, the phase signal ∅2 will always change state when the phase signal ∅1 is a logic high.

It should be understood that the logic circuit described for generating the phase signals ∅1 and ∅2 is provided to illustrate a preferred embodiment of the invention. Other logic circuits which generate phase signals with the indicated non-overlapping relationship can be used, without departing from the invention.

The ∅1 and ∅2 phase signals are applied to an edge detector which includes NAND gates 69, 71 and 73 and inverters 75 and 77. In operation, the positive ∅1 signal is applied to an input of the NAND gate 69 and an inverted, delayed ∅1 signal is applied to an opposite input of the NAND gate 69. The NAND gate 69 generates a negative output pulse with a pulse width defined by the delay provided by the inverter 75. The negative pulse is representative of the leading edge 70 of the ∅1 phase signal.

In a similar manner, the NAND gate 71 and its associated inverter 77 generate a negative pulse that is representative of the trailing edge 74 of the ∅2 phase signal. In operation, the ∅2 signal is applied to one input of the NAND gate 71 and an inverted, delayed signal is applied from the inverter 77 to another input of the NAND gate 71. The output of the NAND gate 71 is high in all cases except at the point of overlap between the trailing edges of the signals applied to the gate. The overlap occurs when the respective signals are a logic high and the NAND gate therefore generates a corresponding negative pulse with a pulse width defined by the delay of the inverter 77.

The negative pulses of the NAND gates 69 and 71 are applied to a NAND gate 73 to force corresponding positive pulses VA at the output of the NAND gate 73.

With reference to the timing diagram of FIG. 4, it can be seen that the VA pulses occur at the leading and trailing edges of the ∅1 and ∅2 signals respectively.

The ∅1 and ∅2 signals are also applied to the inputs of an AND gate 83. The output of this gate is applied to associated OR gates 85 and 87. An opposite input of the OR gate 85 is connected to the Q output of a data flip-flop 89 and an opposite input of the OR gate 87 is connected to the inverted Q output of the flip-flop 89. The input data signal VIN is applied to the data input of the flip-flop 89 and the output of the NAND gate 73 is applied to the clock input of the flip-flop 89. The flip-flop 89 gates the logic level of the signal VIN to the Q output on the leading edge of the VA pulses applied by the NAND gate 73. The inverted Q output of the flip-flop applies a signal inverted with respect to the signal at the Q output.

A representative VIN signal is illustrated at FIG. 4. The particular VIN signal is illustrated to facilitate an explanation of the circuit of the invention. However, it should be understood that any desired VIN signal may be employed, without departing from the invention.

In general, the first level shifter 35 of FIG. 2 generates an output signal VLS1 which has the same polarity as the input signal VIN but which is shifted in voltage level with respect to the voltage level of the signal VIN. Thus, for purposes of discussion, the VIN signal may have a voltage swing, as illustrated at FIG. 1B, between VDD and VSS1. The circuit of FIG. 2 generates a corresponding output signal VLS1 with a greater voltage swing between the voltages VDD and VSS2.

In the circuit of FIG. 3, the logic state of the input signal VIN appears at the output of the data flip-flop 89 only when the flip-flop is gated by the positive VA pulses at the output of the NAND gate 73. The flip-flop 89 thus ensures that changes in the VIN signal are detected in synchronism with the VA pulses.

With reference to FIGS. 3 and 4, if the VIN signal is a logic high, a logic high will be gated through the flip-flop 89 to the Q output and will force a logic high signal VC2 at the output of the OR gate 85. Thus, a gated logic high VIN signal will result in a constant logic high for the VC2 control signal illustrated in the timing diagram of FIG. 4. The flip-flop 89 will also respond to the gated high VIN signal by applying a low logic signal to the OR gate 87. The OR gate 87 will therefore pass VC1 signals generated by the AND gate 83.

When the VIN signal is a logic low, the data flip-flop 89 operates in an opposite manner to force a logic high signal VC1 at the output of the OR gate 87 and to allow the OR gate 85 to pass VC2 signals from the AND gate 83.

The ∅1, ∅2, VA, VC1 and VC2 signals generated by the control circuit of FIG. 3 are applied to operate the strobe circuit 37 and level shifter circuits 35 of FIG. 2. In operation, the VA pulses are applied to inverter transistors P1 and N1 of the strobe circuit 37 and the voltages VDD, VSS1 and VSS2 are applied to the circuit in the manner discussed with respect to the circuit of FIG. 1A. The strobe circuit 37 operates in the manner described for the circuit of FIG. 1A to generate output VALS pulses which have the same polarity and approximately the same timing as the VA signal but which are defined in a voltage range of VDD to VSS2 rather than the voltage range of VDD to VSS1 which was provided for the VA signal. This level translation of the VA signal is required to operate the MOS devices of the level shifters 35.

The operation of the first level shifter 35 illustrated in detail in FIG. 2 will hereafter be explained with respect to the signals generated by the strobe circuit 37 and the control circuit of FIG. 3. It should generally be understood that additional level shifter circuits 35 may be connected to the strobe circuit 37 to provide additional corresponding level translations. However, only one illustrated level shifter circuit 35 is discussed herein in order to facilitate an understanding of the invention.

In operation, the VC1 and VC2 signals are applied to control the operation of the devices P5 and P6 and to therefore determine the logic level of the output VLS1 signal.

With reference to the timing diagram of FIG. 4, the VC1 signal is initially a logic low at point 95 and the VC2 signal is a logic high at a corresponding point 97. With reference to FIG. 2, the logic low of VC1 turns on the device P5 and the corresponding device P7. The device P5 thus conducts to apply the positive VDD voltage to the gate 99 of the device N8 and further defines a positive VDD voltage for the output signal VLS1 on the line 101. The positive signal on the gate 99 of the device N8 turns the device on so that a negative voltage VSS2 is applied at a circuit point 103. The low voltage VSS2 at the circuit point 103 is also applied to a circuit node 107 because the device N7 is turned on as a result of the turning on of the device P7 by the low logic level of VC1. More particularly, when P7 is turned on, it applies a high voltage VDD to the gate 109 of the device N7 and thus causes the device to conduct. The low logic level signal at the node 107 is therefore applied to the gate 111 of the device N6 to turn the device off. Moreover, the device P4 is turned off because of the logic high signal VC2, the N4 and N9 devices are turned off because the VALS signal is a logic low and the device N5 is at an indeterminate state.

When the VC1 signal rises to a logic high at the time 113, the devices P5 and P7 are turned off, but high voltages are maintained at circuit nodes 100 and 102 by capacitance at these nodes and the devices N7 and N8 therefore remain conducting. After VC1 and VC2 are both high, a VALS pulse 115 is generated to turn on the devices N4 and N9 and apply a low VSS2 voltage at nodes 102 and 117. The low voltages at these nodes turn off the devices N5 and N7 but do not affect the output state of the VLS1 signal on the line 101, because as explained above, the voltage at the node 100 is maintained by circuit capacitance. It should be understood that the timing of the VALS signal is determined by the circuit of FIG. 3 to fall within the positive-going VC1 signal. The timing of the control circuit of FIG. 3 therefore ensures that both devices P4 and P7 are turned off by respective highs of VC1 and VC2 before the VALS signal is generated to turn on the devices N4 and N9. Thus, the devices N4 and N9 are turned on without shorting the devices P4 and P7. After the VALS signal 115 drops to a logic low, the VC1 signal also drops to a logic low to again turn on the devices P5 and P7 so that a high voltage is maintained at the circuit node 100 to firmly hold the output signal VLS1 at a positive logic level.

With reference to the timing diagram of FIG. 4, it can be seen that successive VALS signals 119, 121 and 123 are generated within corresponding positive pulses of the VCI signal to maintain a positive voltage for the output signal VLS1. Thus, it should be appreciated that the circuit of FIG. 2 operates to maintain a constant logic high signal for VLS1, while maintaining the low level of static current consumption which is characteristic of CMOS logic.

As explained above, the circuit of FIG. 3 applies VA pulses to strobe changes in the logic level of the VIN data signal. Thus, the circuit of FIG. 3 recognizes logic level changes in the VIN status signal only at the time that VA pulses occur. Accordingly, with reference to the timing diagram of FIG. 4, the VIN data signal may change its logic state at any time between successive VA pulses. In view of the fact that the timing of the VALS level shifted pulses is the same as the VA pulses, reference will hereafter be made to the timing of VALS pulses, with the understanding that, with respect to FIG. 3, the corresponding VA pulses provide the required gating functions.

With reference to FIG. 4, the VIN data signal may change its logic state at any time between successive VALS pulses and the change in state will be recognized by the circuit of FIG. 3 only at the time that VALS pulses occur. Thus, for example, the state of the VIN signal may change at any time between successive VALS pulses 123 and 127. For simplicity of illustration, the timing diagram of FIG. 4 illustrates changes in VIN which occur at the time of generation of VALS pulses. It should generally be understood that this timing illustration is provided to facilitate an understanding of the invention and is not intended to suggest that VIN may change only during the occurrence of VALS pulses. As stated above, changes in logic state of the VIN signal occur asynchronously and the changes are synchronously strobed by the VA pulses, which correspond in timing to the VALS level shifted pulses.

As illustrated in FIG. 4, the VIN data signal drops to a low logic level at the timing point 125. The change in state of the VIN signal is strobed by the VA pulse which corresponds to the VALS pulse 127. The data flip-flop 89 stores the change in logic level of the VIN data signal and applies the stored logic level to control the state of the VC1 and VC2 signals.

It should be understood that the circuit of FIG. 3 ensures that VALS pulses are generated only when the VC1 and VC2 signals are both a logic high. This system constraint is achieved by defining non-overlapping ∅1 and ∅2 phase signals to generate the VALS pulses and to control the logic level of the VC1 and VC2 signals. Thus, as shown in the timing diagram of FIG. 4, the VALS pulse 127 is generated at the designated points in time 129 when the ∅1 and ∅2 signals are a logic high. The AND gate 83 of FIG. 3 applies the logic states of the ∅1 and ∅2 signals to control the logic state of the VC1 and VC2 signals. Thus, with reference to FIG. 4, simultaneous logic high levels for the ∅1 and ∅2 signals force a logic high for both the VC1 and VC2 signals. This is important, because the VC1 and VC2 signals control the devices P5 and P6 which determine the logic state of the output signal VLS1. If the VC1 and VC2 signals are both high, the devices P5 and P6 are turned off and therefore do not drive their respective circuit nodes 100 and 107 to a logic high VDD voltage.

The timing circuit of FIG. 3 thus ensures that the devices P5 and P6 will be turned off by simultaneous high logic signals for VC1 and VC2 when each VALS signal is generated. The VALS signals each turn on the devices N4 and N9 to apply a logic low voltage VSS2 to the circuit nodes 117 and 102. The low at the nodes 117 and 102 turns off the devices N5 and N7 and therefore disconnects the device P5 from the device N6 and the device P6 from the device N8.

With reference to the timing diagram of FIG. 4 and to the circuit of FIG. 2, when the VIN data signal drops to a logic low at 125 and the VALS pulse is generated, the devices N4 and N9 are turned on to apply a negative VSS2 voltage at the nodes 117 and 102 and to therefore turn off the devices N5 and N7. As explained previously, the VALS pulse 127 is generated at a time when VC1 and VC2 are a logic high and therefore the devices P4, P5, P6 and P7 are turned off so that the negative voltages at the points 117 and 102 are not shorted to the positive voltage VDD.

Just prior to the generation of the VALS pulse 127, the VC1 signal was a logic low and the VC2 signal was a logic high. The low VC1 signal turned on the devices P5 and P7 and thus applied a positive voltage VDD at the circuit nodes 100 and 102. The positive voltage at the node 100 turned on the device N8 and thus applied a negative voltage VSS2 to the circuit point 103. The positive voltage at the circuit node 102 turned on the device N7 and thus applied the negative voltage at 103 to circuit node 107 and to the gate 111 of the device N6 to turn off the device N6. Thus, at the point in time at which the VALS pulse 127 is generated, the signals VC1 and VC2 are a logic high and a positive voltage is maintained by capacitance at the circuit node 100 to keep the device N8 turned on and to maintain a negative voltage at the circuit point 103 and the circuit node 107.

When the VALS signal 127 is completed at the timing point 131, the logic levels of the VC1 and VC2 signals are adjusted by the circuit of FIG. 3 to reflect the changed logic state of the VIN data signal. Thus, the low VIN data signal causes the VC1 signal to be held at a logic high and allows the VC2 signal to change logic state in accordance with the logic states of the ∅1 and ∅2 signals which drive the AND gate 83. At the timing point 131, the VC2 signal is a logic low, as a result of the low signal occurring at that time for ∅2.

The low logic level of VC2 turns on the devices P6 and P4. The conducting device P6 applies a positive voltage VDD to the circuit node 107. The device P6 does not have to overcome the conducting device N8, because the VALS pulse 127 previously turned on the device N9 and thus applied a low voltage at the circuit node 102 to turn off the device N7. The device N7 disconnected the device P6 from the device N8. Accordingly, when P6 was turned on by the low logic level of VC2, the device N8 was disconnected from P6 and therefore did not resist the application of a positive voltage VDD to the circuit node 107. Moreover, the low logic level of VC2 turned on the device P4 and therefore applied a positive voltage at circuit node 117 without difficulty, because the device N4 was turned off as a result of the low logic level on the gate of the device N4.

The high logic level at the node 107 turns on the device N6 and therefore applies the negative voltage VSS2 to the circuit node 100 through the conducting device N5. The low voltage at the circuit node 100 is applied to turn off the device N8 and to further supply a strong negative voltage VSS2 for the output signal VLS1. Thereafter, for as long as the VIN data signal maintains its low logic level, the signal VLS1 is maintained at a low logic voltage VSS2. As described previously, the VC1 and VC2 signals are periodically simultaneously raised to a high level, in this instance by raising the logic level of the VC2 signal, in order to accommodate the generation of a VALS pulse. While the VALS pulse is being generated, the high logic levels at circuit nodes 107 and 117 are maintained by the capacitance of the nodes. After each VALS pulse is completed, a low logic level is again provided by the VC2 signal and the circuit of FIG. 2 again strongly latches to provide a negative voltage VSS2 for VLS1.

It should now be understood that when the VIN data signal changes its logic state to a logic high between VALS pulses 135 and 137, the VA pulse corresponding to the VALS pulse 137 will strobe the logic change into the flip-flop 89 of FIG. 3 to initiate the respective adjustments of the VC1 and VC2 signals. At the time that the VALS pulse 137 is generated, the VC1 and VC2 signals are maintained at a logic high and the VALS pulse 137 is applied to turn on the device N4 and turn off the device N5. The device N5 disconnects the devices P5 and N6 and therefore allows the logic low of the VC1 signal at timing point 139 to turn on the device P5 and apply a positive voltage VDD to the circuit node 100 without fighting the conducting device N6. The level shifter 35 of the circuit of FIG. 2 is then operated in the manner described above to turn on the device N8 and turn off the device N6 to provide a negative voltage VSS2 for VLS1 and a positive voltage VDD for the inverted signal VLSI1.

It should now be understood that the level shifter 35 of the circuit of FIG. 2 operates to receive an input logic signal VIN with a voltage swing from VSS1 to VDD and generates a corresponding output signal VLS1 of the same polarity with a greater voltage swing from VSS2 to VDD. In operation, the circuit of FIG. 2 periodically applies a VALS pulse to turn off devices N5 and N7 by pulling their gates low with N4 and N9 respectively. The turning off of the devices N5 and N7 eliminates any series conducting path from voltage nodes 100 and 107 and devices P5,P6 (which define VLS1 and VLSI1) to the negative voltage VSS2. The non-overlapping relationship of control signals VC1 and VC2 ensures that VC1 and VC2 are both a logic high when each VALS pulse is generated and therefore the devices P5 and P6 are turned off when the VALS signal turns off the devices N5 and N7 and disconnects P5 and P6 from their respective associated devices N6 and N8. The circuit of FIG. 2 therefore initiates a change in the logic state of the output signal VLS1 only after control input devices P5 and P6 are disconnected from their associated control output devices N6 and N8.

It should now be appreciated that in operation of the level shifter 35 of FIG. 2, no DC current path is ever established between VDD and VSS2 and further, only voltages maintained by node capacitance are charged or discharged. This advantageous operation ensures that the feed-through current spike described for the prior art circuit of FIG. 1A is eliminated, thus reducing the dynamic current consumption of the improved circuit of FIG. 2. Moreover, although more transistors are required for the circuit of FIG. 2 than for the prior art circuit of FIG. 1A, the circuit of FIG. 2 does not require the use of transistors with large Z/L ratios and therefore may be implemented with a much smaller, preferably minimum geometry. The circuit of FIG. 2 also has the design advantage that output logic levels are maintained by CMOS devices during most of the cycle of operation of the circuit (i.e., except during the relatively narrow VALS pulses). This operation results in a strongly driven output signal which is generally not susceptible to leakage effects. Moreover, the circuit of FIG. 2 operates as a latch and therefore, if the input clock to the circuit of FIG. 3 stops, the output of the level shifter will remain at its last defined state and will not float.

The circuit of FIG. 2 therefore provides an improved, low current CMOS level shifter. The circuit uses dynamic logic techniques to reduce DC switching currents and to minimize the size of transistors and therefore the overall size of the circuit.

Although a particular preferred embodiment of the level shifter circuit 35 of FIG. 2 and of an associated control circuit of FIG. 3 has been disclosed, it should be understood that other circuits and components may be used to achieve the objects of the invention, without departing from the spirit of the invention. Thus, the invention may be embodied in other specific forms without departing from its spirit or essential characteristics. The present embodiments are, therefore, to be considered in all respects as illustrative and not restrictive. The scope of the invention is indicated by the claims rather than by the foregoing description. All changes which come within the meaning and range of the equivalents of the claims are intended to be embraced therein.

I claim:

1. A voltage level shifter for receiving an input signal having a predetermined magnitude of voltage and generating an output signal having a different magnitude of voltage, comprising:
   a first input transistor for turning on to conduct in response to a first of two logic states of said input signal and for turning off in response to the second of said logic states;
   a second input transistor for turning on to conduct in response to the second of said two logic states of said input signal and for turning off in response to the first of said logic states;
   a first output transistor connected to said first input transistor for turning on to conduct when said first input transistor is conducting and for generating said output signal at the point of connection of the transistors;
   a second output transistor connected to said second input transistor for turning on to conduct when said second input transistor is conducting and for generating the inverse of said output signal at the point of connection of the transistors;
   a first reset transistor connected between said first input transistor and said second output transistor for selectively turning on to connect said first input and said second output transistors and for selectively turning off to disconnect the first input and second output transistors;
   a second reset transistor connected between second input transistor and said first output transistor for selectively turning on to connect said second input and said first output transistors and for selectively turning off to disconnect said second input and first output transistors; and
   control means for turning off said first and second reset transistors prior to turning on one of said input transistors in response to a change in the logic state of said input signal, said control means including means for thereafter turning on said one input transistor and said first and second reset transistors to effectuate a change of output logic state.

2. The voltage level shifter of claim 1, wherein said control means includes means for periodically turning off said first and second input transistors for a predefined time and turning off said reset transistors for at least a portion of said time, said control means including means for thereafter allowing the input transistors to respond to the logic states of said input signal.

3. The voltage level shifter of claim 1, wherein said control means includes:
   means for periodically generating a reset control signal;
   a first reset control transistor connected to said first reset transistor for turning on in response to the second logic state of said input signal and thereby turning on said first reset transistor;
   a second reset control transistor connected to said second reset transistor for turning on in response to the first logic state of said input signal and thereby turning on said second reset transistor;
   a third reset control transistor connected to said first reset transistor for turning the first reset transistor off in response to said reset control signal;
   a fourth reset control transistor connected to said second reset transistor for turning the second reset transistor off in response to said reset control signal; and
   means for turning off said first and second input transistors and said first and second reset control transistors when said reset control signal is generated.

4. The voltage level shifter of claim 3, wherein said first and second input transistors and said first and second reset control transistors are P-type field-effect transistors and said output, reset and third and fourth reset control transistors are N-type field-effect transistors.

5. The voltage level shifter of claim 4, wherein said P-type transistors have a Z/L ratio of 10/5 and the N-type transistors have a Z/L ratio of 5/5.

6. A voltage level shifter for receiving an input signal having a predetermined magnitude of voltage and generating an output signal having a different magnitude of voltage, comprising:
   a first input transistor for turning on to conduct in response to a first of two logic states of said input signal and for turning off in response to the second of said logic states;
   a second input transistor for turning on to conduct in response to the second of said two logic states of said input signal and for turning off in response to the first of said logic states;
   a first output transistor connected to said first input transistor for turning on to conduct when said first input transistor is conducting and for generating said output signal at the point of connection of the transistors;
   a second output transistor connected to said second input transistor for turning on to conduct when said second input transistor is conducting and for generating the inverse of said output signal at the point of connection of the transistors;
   a first reset transistor connected between said first input transistor and said second output transistor for selectively turning on to connect said first input and said second output transistors and for selectively turning off to disconnect the first input and second output transistors;
   a second reset transistor connected between said second input transistor and said first output transistor for selectively truning on to connect said second input and said first output transistiors and for selectively turning off to disconnect said second input and first output transistors; and control means for turning off said first and second reset transistors prior to turning on one of said input transistors in response to a change in the logic state of said input signal, said control means including means for thereafter turning on said one input transistor and at least one of said reset treansistors so that the output transistor which was turned off and the other input transistor which was turned on prior to the change of logic state of the input signal are connected to effectuate a change of output logic state.

7. The voltage level shifter of claim 6, wherein said control means includes means for periodically turning off said first and second input transistors for a predefined time and turning off said reset transistors for at least a portion of said time, said control means including means for thereafter allowing the input transistors to respond to the logic states of said input signal.

8. The voltage level shifter of claim 6, wherein said control means includes:

means for periodically generating a reset control signal;

a first reset control transistor connected to said first reset transistor forturning on in response to the second logic state of said input signal and thereby turning on said first reset transistor;

a second reset control transistor connected to said second reset transistor for turning on in response to the first logic state of said input signal and thereby turning on said second reset transistor;

a third reset control transistor connected to said first reset transistor for turning the first reset transistor off in response to said reset control signal;

a fourth reset control transistor connected to said second reset transistor for turning the second reset transistor off in response to said reset control signal; and means for turning off said first and second input transistors and said first and second reset control transistors when said reset control signal is generated.

9. The voltage level shifter of claim 8, wherein said first and second input transistors and said first and second reset control transistors are P-type field-effect transistors and said output, reset and third and fourth reset control transistors are N-type filed-effect transistors.

10. The voltage level shifter of claim 9, wherein said P-type transistors have a Z/L ratio of 10/5 and the N-type transistors have a Z/L ratio of 5/5.

11. A voltage level shifter for receiving an input signal having a predetermined magnitude of voltage and generating an output signal having a different magnitude of voltage, comprising:

a first input transistor for turning on to conduct in response to a first of two logic states of said input signal and for turning off in response to the second of said logic states;

a second input transistor for turning on to conduct in response to the second of said two logic states of said input signal and for turning off in response to the first of said logic states;

a first output transistor connected to said first input transistor for turning on to conduct when said first input transistor is conducting and for generating said output signal at the point of connection of the transistors;

a second output transistor connected to said second input transistor for turning on to conduct when said second input transistor is conducting and for generating the inverse of said output signal at the point of connection of the transistors;

a first reset transistor connected between said first input transistor and said second output transistor for selectively turning on to connect said first input and said second output transistors and for selectively turning off to disconnect the first input and second output transistors;

a second reset transistor connected between second input transistor and said first output transistor for selectively turning on to connect said second input and said first output transistors and for selectively turning off to disconnect said second input and first output transistors; and control means for turning off at least one of said reset transistors prior to turning on one of said input transistors in response to a change in the logic state of said input signal, so that the output transistor which is turned on and said one input transistor which is turned off prior to said change in logic state are disconnected;

said control means including means for thereafter turning on said one input transistor and said first and second reset transistors to effectuate an output logic state change.

12. The voltage level shifter of claim 11, wherein said control means includes means for periodically turning off said first and second input transistors for a predefined time and turning off said reset transistors for at least a portion of said time, said control means including means for thereafter allowing the input transistors to respond to the logic states of said input signal.

13. The voltage level shifter of claim 11, wherein said control means includes:

means for periodically generating a reset control signal;

a first reset control transistor connected to said first reset transistor for turning on in response to the second logic state of said input signal and thereby turning on said first reset transistor;

a second reset control transistor connected to said second reset transistor for turning on in response to the first logic state of said input signal and thereby turning on said second reset transistor;

a third reset control transistor connected to said first reset transistor for turning the first reset transistor off in response to said reset control signal;

a fourth reset control transistor connected to said second reset transistor for turning the second reset transistor off in response to said reset control signal; and means for turning off said first and second input transistors and said first and second reset control transistors when said reset control signal is generated.

14. The voltage level shifter of claim 13, wherein said first and second input transistors and said first and second reset control transistors are P-type field-effect transistors and said output, reset and third and fourth reset control transistors are N-type field-effect transistors.

15. The voltage level shifter of claim 14 wherein said P-type transistors have a Z/L ratio of 10/5 and the N-type transistors have a Z/L ratio of 5/5.

16. A voltage level shifter for receiving an input signal having a predetermined magnitude of voltage and generating an output signal having a different magnitude of voltage, comprising:
- a first input transistor for turning on to conduct in response to a first of two logic states of said input signal and for turning off in response to the second of said logic states;
- a second input transistor for turning on to conduct in response to the second of said two logic states of said input signal and for turning off in response to the first of said logic states;
- a first output transistor connected to said first input transistor for turning on to conduct when said first input transistor is conducting and for generating said output signal at the point of connection of the transistors;
- a second output transistor connected to said second input transistor for turning on to conduct when said second input transistor is conducting and for generating the inverse of said output signal at the point of connection of the transistors;
- a first reset transistor connected between said first input transistor and said second output transistor for selectively turning on to connect said first input and said second output transistors and for selectively turning off to disconnect the first input and second output transistors;
- a second reset transistor connected between said second input transistor and said first output transistor for selectively turning on to connect said second input and said first output transistors and for selectively turning off to disconnect said second input and first output transistors; and
- control means for turning off one of said reset transistors prior to turning on one of said input transistors in response to a change in the logic state of said input signal, so that the output transistor which is turned on and said one input transistor which is turned off prior to said change in logic state are disconnected,
- said control means including means for thereafter turning on said one input transistor and the other of said reset transistors, so that the output transistor which was turned off and the input transistor which was turned on prior to the change of state of the input signal are connected to effectuate a change of output logic state.

17. The voltage level shifter of claim 16, wherein said control means includes means for periodically turning off said first and second input transistors for a predefined time and turning off said reset transistors for at least a portion of said time, said control means including means for thereafter allowing the input transistors to respond to the logic states of said input signal.

18. The voltage level shifter of claim 16, wherein said control means includes:
- means for periodically generating a reset control signal;
- a first reset control transistor connected to said first reset transistor for turning on in response to the second logic state of said input signal and thereby turning on said first reset transistor;
- a second reset control transistor connected to said second reset transistor for turning on in response to the first logic state of said input signal and thereby turning on said second reset transistor;
- a third reset control transistor connected to said first reset transistor for turning the first reset transistor off in response to said reset control siganl;
- a fourth reset control transistor connected to said second reset transistor for turning the second reset transistor off in response to said reset control signal; and
- means for turning off said first and second input transistors and said first and second reset control transistors when said reset control signal is generated.

19. The voltage level shifter of claim 18, wherein said first and second input transistors and said first and second reset control transistors are P-type field-effect transistors and said output, reset and third and fourth reset control transistors are N-type field-effect transistors.

20. The voltage level shifter of claim 19, wherein said P-type transistors have a Z/L ratio of 10/5 and the N-type transistors have a Z/L ratio of 5/5.

* * * * *